United States Patent [19]
Keller

[11] Patent Number: 4,650,814
[45] Date of Patent: Mar. 17, 1987

[54] PROCESS FOR PRODUCING METHANOL FROM A FEED GAS

[76] Inventor: Arnold P. Keller, 8226 Furlong La., Houston, Tex. 77071

[21] Appl. No.: 833,565

[22] Filed: Feb. 24, 1986

Related U.S. Application Data

[63] Continuation of Ser. No. 587,057, Mar. 7, 1984, abandoned.

[51] Int. Cl.$^4$ .............................................. C07G 27/06
[52] U.S. Cl. ..................................... 518/703; 518/705
[58] Field of Search ........................ 518/705, 703, 704

[56] References Cited

U.S. PATENT DOCUMENTS 4,130,403  12/1978  Cooley et al. .
4,180,553  12/1979  Null et al. .
4,181,675   1/1980  Makin et al. .
4,264,338   4/1981  Null .

FOREIGN PATENT DOCUMENTS 57-95926  6/1982  Japan .

OTHER PUBLICATIONS

Cornelius et al., "Methanol and Electrical Power from U.S. Coals Using Lurgi Gasification," a paper presented at Coal Technology, 1982, Dec. 7–9, 1982.
Burmaster et al., "Increased Methanol Production Using PRISM ® Separators," paper presented at National AICHE Meeting, Mar. 27–31, 1983.
Tart et al., "Methanation Key to SNG Success," Hydrocarbon Processing, Apr. 1981, pp. 114–118.
Van Gelder, "Hydrogen Recovery from Ammonia Plant Purge Gas Via PRISM ® Separators," paper presented at Technical Conference on Ammonia Fertilization Technology, Peking, China, Mar. 13–28, 1982.

*Primary Examiner*—Howard T. Mars
*Attorney, Agent, or Firm*—Arnold, White & Durkee

[57] ABSTRACT

There is provided a process for producing a hydrocarbon product from a feed gas by passing at least a portion of a feed gas stream comprising hydrogen and carbon monoxide to a first separation zone and physically separating the feed gas stream, as for example by use of a membrane, into a first hydrogen stream wherein the ratio of hydrogen to carbon monoxide is greater in the feed gas stream and thereafter passing the first hydrogen stream to a product reaction zone to form a mixed product stream, which in turn undergoes physical separation to form a second hydrogen stream for selective recycle to the product reaction zone and a product stream including a hydrocarbon product such as methanol or methane.

12 Claims, 3 Drawing Figures

PROCESS FOR PRODUCING METHANOL FROM A FEED GAS

This is a continuation of co-pending application Ser. No. 587,057 filed on Mar. 7, 1984 now abandoned.

BACKGROUND OF THE INVENTION

This invention relates to a process for producing a hydrocarbon product from a feed gas and more particularly to a process for producing a hydrocarbon product or methanol from a feed gas stream comprising hydrogen and carbon monoxide.

The carbon monoxide conversion or shift reaction may be written as follows:

$$CO + H_2O = CO_2 + H_2$$

The reaction is exothermic, such that an increase in temperature decreases the conversion of carbon monoxide to carbon dioxide.

The carbon monoxide conversion or shift reaction plays a part in a number of chemical processes including those involving reactions between hydrocarbons such as methane or propane and steam in the production of hydrogen. For example, in one method of producing hydrogen from methane, or propane, methane or propane vapors are mixed with steam and catalytically reformed at high temperatures to produce a gas comprising hydrogen, carbon monoxide, carbon dioxide, and any unconsumed reactants. The gas is cooled and the partial pressure of the water vapor is increased by the addition of steam. The resultant mixture is passed over a catalyst in a carbon monoxide shift converter, where a substantial percentage of the carbon monoxide is converted to carbon dioxide with more hydrogen being produced as a result of the CO shift reaction.

The synthesis reaction also plays a part in chemical processes employing synthesis gas, which is generally made up of hydrogen, oxides of carbon, and possibly other constituents such as nitrogen. Synthesis gas may be produced by a variety of methods, including steam hydrocarbon reforming, auto reforming, and the gasification of coal. The resulting synthesis gas is useful in a variety of processes, including the production of methane, methanol, hydrogen, ammonia and other products However, efficiency often requires adjustment of the relative amount of hydrogen to carbon monoxide present in a given system at various stages. For example, in the manufacture of methanol from a synthesis gas comprising hydrogen and the oxides of carbon the ratio of hydrogen to the oxides of carbon must generally be adjusted to provide a favorable stoichiometric relationship. This adjustment is accomplished by use of the carbon monoxide shift reaction in a high temperature shift reactor supplied with steam, followed by the removal of excess carbon dioxide in an acid gas treating unit.

Similarly, in the production of a synthetic natural gas comprising methane from carbon monoxide and hydrogen, the production of methane is generally favored by particular hydrogen to carbon monoxide stoichiometric ratios However, many synthesis gases produced from coal gasification or other processes contain too little hydrogen in relation to the carbon monoxide present to be directly effective in the production of methane. Consequently, the feed gas is generally adjusted by using the carbon monoxide shift reaction on part or all of the synthesis feed gas followed by removal of excess carbon dioxide, if appropriate, to provide the desired ratio of feed components to the methanation process.

A number of processes disclosed in the literature attempt to reduce the part played by the CO shift reaction. For example, in Tart, K. R. et al., "Methanation Key to SNG Success", Hydrocarbon Processing, (April 1981), p. 114, et seq. there is disclosed a methanation process using a synthesis gas produced from coal gasification. A slagging gasifier is fed batchwise with a coal feed. A mixture of steam and oxygen are used in the gasifier to produce hot gaseous products The product gas from the slagging gasifier is said to have a hydrogen to carbon monoxide ratio of about 0.5. As the desired hydrogen to carbon monoxide ratio is generally between 1 and 3, the product gas from the gasifier may require a catalytic carbon monoxide shift conversion prior to chemical synthesis to obtain the desired hydrogen to carbon monoxide ratio. Alternatively, as disclosed in the article, CO-shift conversion and methane synthesis can be accomplished simultaneously over a single catalyst.

As indicated in that article, as a result of the process a separate CO shift stage with all its ancillary equipment is no longer needed. According to this method purified synthesis gas enters a saturator in which it is contacted with a countercurrent flow of water that has been heated by indirect heat exchange with gas streams within the process. This arrangement is said to utilize otherwise unusable low grade heat for provision of process steam and is also said to make a substantial contribution to the efficiency of the process. Saturated feed gas then undergoes direct methane synthesis in a series of catalytic reactors, the outlet temperatures of which are controlled by recycle of cooled product gas. The heat released from the highly exothermic synthesis reactions is used to generate high pressure steam for export to other process stages. Final methanation, gas cooling and carbon dioxide removal and drying are said to yield a synthetic natural gas containing less than 3% hydrogen and 0.1% carbon monoxide.

Another method produces methanol from gases produced in a Lurgi fixed bed gasification process. Coal, oxygen and steam are supplied to the gasifier in such quantities so as to cause the CO shift reaction to proceed inside the gasifier and to produce a crude gas in which the hydrogen to carbon monoxide ratio of the crude gas already meets the desired hyrogen to carbon monoxide ratio. The gas is cleaned, treated for removal of acid gases and is ultimately fed to a methanol reactor recycle loop. However, because the CO shift reaction occurs in the gasifier, without the aid of a catalyst, it is understood that the gasifier needs more steam than is required in a combination of slagging gasifier followed by steam addition prior to an external catalytic shift reactor.

The literature also discloses a number of processes using separation membranes in conjunction with chemical processes. For example, Null, U.S. Pat. No. 4,264,338 discloses a process for the separation of gases by selective membrane diffusion or permeation without increasing the work required. This is said to be accomplished by directing a permeate mixture from a second or later stage of separation to a recycle stage of membrane separation to provide a permeate enriched in the desired gas or gases. This step is followed by blending the permeate with the gaseous feed to the second or later stage of separation.

Null, et al., U.S. Pat. No. 4,180,553 discloses an ammonia synthesis process utilizing a separation membrane. In the process a purge stream from an ammonia synthesis loop is contacted at above atmospheric pressure with the feed side of a separation membrane which exhibits selected permeation of each of hydrogen and ammonia as compared to the permeation of each of methane and nitrogen. A total pressure differential across the membrane is maintained to provide a driving force for the permeation of hydrogen and ammonia through the membrane A hydrogen-rich permeating gas which contains ammonia is obtained on the permeate exit side of the membrane. Permeating gas is combined with the gas in the ammonia synthesis loop and passed to an ammonia reaction zone for conversion to ammonia.

Other methods use membrane separators in a variety of processes. For example, one process uses membranes to recover hydrogen and carbon oxides from a methanol synthesis purge stream leaving a methanol reactor. The hydrogen and oxides of carbon are recycled as feed for the methanol reactor.

These and other processes utilizing a feed stream comprising hydrogen and carbon monoxide to produce a hydrocarbon product or energy or both suffer from one or more of several defects or limitations. For example, prior processes using the shift reaction to obtain appropriate ratios of hydrogen to carbon monoxide introduce large amounts of carbon dioxide which subsequently must be removed from the system. Other processes require the use of purge steams taking off a material portion of reactants when recycle is used. Further, additional steam over and above that consumed in the reaction must often be generated. This is to force the equilibrium constant in favor of hydrogen and carbon dioxide; and, also to prevent excessive temperature rise across the reactor. Any recovered condensate containing acid gases must be subsequently purified prior to reuse in a steam generator.

These and other disadvantages or limitations are substantially minimized, if not eliminated, by the present invention.

SUMMARY OF THE INVENTION

There is provided a process for producing a hydrocarbon product or methanol from a feed gas. The feed gas stream includes hydrogen and carbon monoxide. The ratio of hydrogen to carbon monoxide in the feed gas stream is generally greater than about 0.5, but less than about 3.0. The feed gas stream is passed through a first separation zone and the feed gas is physically separated in that zone into a first hydrogen stream wherein the ratio of hydrogen to carbon monoxide is greater than in the feed gas stream and generally in the range of about 0.6 to about 3.0. A hydrogen lean stream rich in carbon monoxide is also produced in the first separation zone with the term "rich" referring to the fact that the relative ratio of carbon monoxide to hydrogen is greater than in the feed. The hydrogen lean stream produced in the first separation zone is a useful second product from the process.

The first hydrogen stream is passed to a product reaction zone to form methanol by the reaction of reactants including hydrogen and carbon monoxide. A residual stream is also formed that includes by-product and residual hydrogen and carbon monoxide. The ratio of hydrogen to other reactants in the product reaction zone is such as to facilitate the formation of the product.

The product, by-product, and residual hydrogen and carbon monoxide are removed as a mixed product stream from the product reaction zone. The product and residual stream are then physically separated from the mixed product stream in a second separation zone to form at least two separate streams including a product stream and a second hydrogen stream. The second hydrogen stream includes hydrogen and maybe some carbon monoxide. At least a portion of the second hydrogen stream and, if appropriate any portion of the feed gas stream not passed to the first separation zone, are used to adjust and maintain the ratio of the reactants in the product reaction zone at a predefined stoichiometric ratio to facilitate formation of methanol in the product reaction zone. For example, the ratio of hydrogen to carbon oxides may be maintained at a desired ratio.

The first and second separation zones preferably include at least one membrane separator, but may include another physical separating device such as appropriately engineered pressure swing adsorbers.

In one embodiment there is provided a process for producing methanol as the product. At least a portion of a feed gas stream including hydrogen and carbon monoxide and substantially free of sulfur is passed to a first separation zone having one or more membrane separators or other physical separating device such as an appropriately engineered pressure swing adsorber system. The ratio of hydrogen to carbon monoxide in the feed gas stream is usually in the ratio of about 0.5 to 2.0. The feed gas stream is preferably at a pressure in the range of about 200 to 1500 psia and more preferably at the higher end of that range. The feed gas stream entering the first separation zone is separated in the separation zone into a first hydrogen rich stream and a first hydrogen lean stream rich in carbon monoxide. The first hydrogen rich stream is passed to a product reaction zone at a sufficient temperature and pressure to form a mixed product stream. The mixed product stream includes methanol, water and any unreacted reactants, including hydrogen and oxides of carbon. The ratio of hydrogen to carbon monoxide plus one and a half times carbon dioxide in the product reaction zone is preferably in the range of about 2.0 to 2.1 to thereby facilitate the formation of methanol with the minimum amount of unwanted side reactions.

The temperature of the resulting mixed product stream is reduced to condense out methanol and water as a product stream and a residual stream including hydrogen. Any remaining methanol is substantially removed from the residual stream. The residual stream is thereafter passed to a second separation zone including at least one membrane separator or other physical separating device such as an appropriately engineered pressure swing adsorber to form a second rich hydrogen stream and a second lean hydrogen stream rich in carbon monoxide. At least a portion of the second hydrogen rich stream is recycled to the product reaction zone. The second hydrogen rich stream and any portion of the feed gas stream not passed to the first separation zone are used to adjust and maintain the predetermined ratio of reactants in the product reaction zone. For example, the second hydrogen rich stream may be used to maintain the ratio of hydrogen to carbon monoxide plus one and a half times carbon dioxide in the range of about 2.0 to 2.1, to thereby facilitate the formation of methanol in the product reaction zone.

In another embodiment there is provided a process for producing a hydrocarbon product comprising methane. A feed gas stream comprising hydrogen and carbon monoxide is supplied to a first separation zone. The ratio of hydrogen to carbon monoxide in the feed gas stream is greater than about 0.5 but less than about 3.0. The feed gas stream is separated in the first separation zone into a first hydrogen rich stream including hydrogen and carbon monoxide and a first hydrogen lean stream rich in carbon monoxide. The first hydrogen rich stream is passed to a product reaction zone to form a first mixed product stream including methane, carbon dioxide and water along with unreacted hydrogen and carbon monoxide. Hydrogen, carbon monoxide, and methane are then recovered from the first mixed product stream as for example by cooling and condensing the water vapor, and by removing carbon dioxide in a carbon dioxide removal plant, to form a second mixed product stream including methane, carbon monoxide and hydrogen. The second mixed product stream is then passed to a second separation zone to form a product stream including methane, and a hydrogen rich stream comprising hydrogen, and carbon monoxide as well as any residual carbon dioxide, and some methane.

A more detailed description of the present invention will now be provided with reference to the foregoing drawings. This description is to be taken by way of illustration rather than limitation.

DETAILED DESCRIPTION

Figure 1:
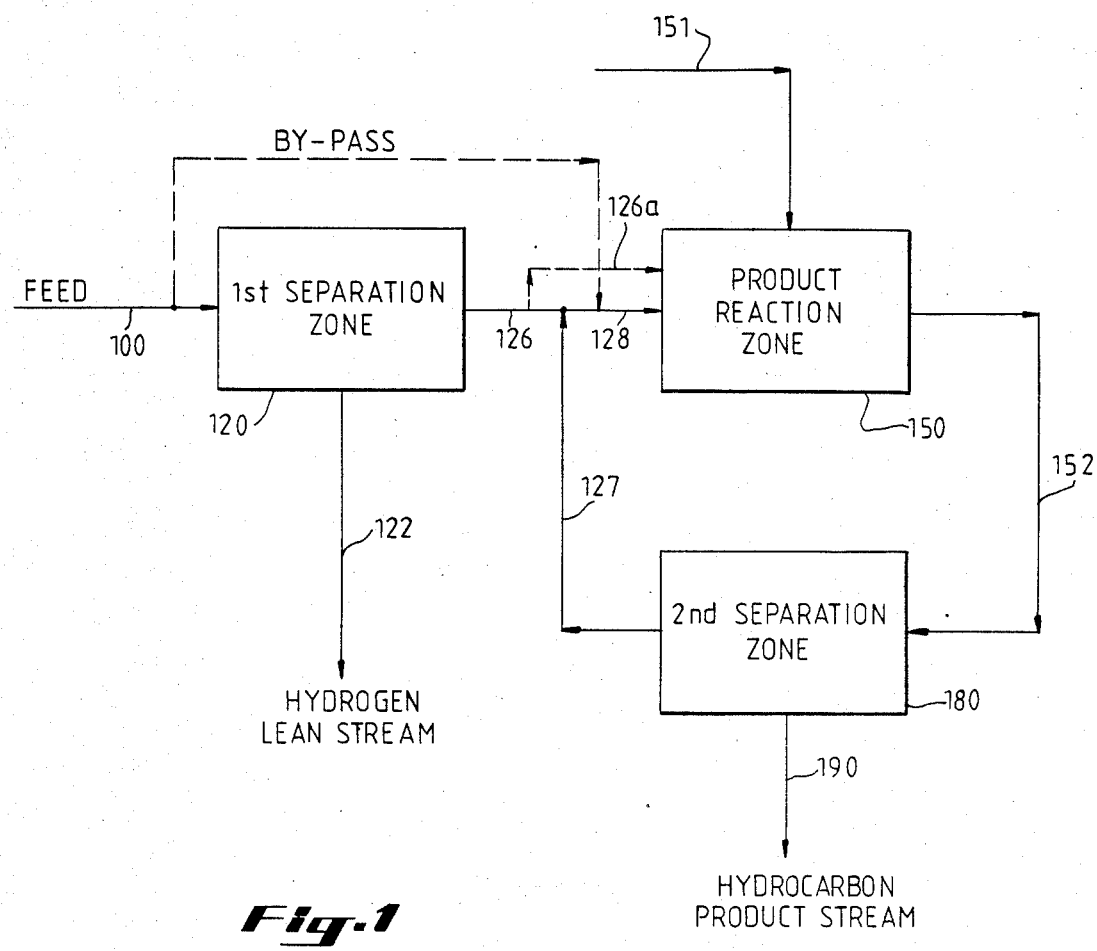
FIG. 1 is a flow diagram of a broad embodiment of the present invention.

As shown generally in FIG. 1, a feed gas stream 100 is passed to a first separation zone 120. The feed gas stream is made up of a gas such as a synthesis feed gas which includes hydrogen and carbon monoxide in a ratio of hydrogen to carbon monoxide greater than about 0.5 but less than about 3.0. (All ratios and percentages are in moles unless otherwise indicated.) The ratio of hydrogen to carbon monoxide will vary depending upon the particular product desired and the process conditions. By way of example, if the desired product is methanol, the ratio of hydrogen to carbon monoxide plus one and a half times carbon dioxide needs to be adjusted in the reaction zone to range from about 2.0 preferably to about 2.1, while if the ultimate product desired is methane, the ratio of hydrogen to carbon monoxide in the reaction zone needs to be adjusted to range from about 1.0 to 3.0, but preferably as close to 3.0 as possible.

The first separation zone includes at least one membrane separator or other separating device for physically separating the feed gas stream into a first hydrogen stream 126 and a hydrogen lean stream 122. The first hydrogen stream 126 has a ratio of hydrogen to carbon monoxide greater than in the feed gas stream and preferably in the range of about 1.0 to about 3.0. The hydrogen lean stream 122 is rich in carbon monoxide in relation to the feed gas stream.

The ratio of hydrogen to carbon monoxide in the first hydrogen stream may be further adjusted if desired or necessary by mixing the first hydrogen stream 126 with gas from recycle stream 127 to form reactant stream 128. Additionally, a portion of the first hydrogen stream in line 126 may pass via line 126a to a different portion of the product reaction zone, if desired. Any additional reactants required may be passed via line 151 to the product reaction zone 150. For example, if the desired product is methanol the ratio of hydrogen to carbon monoxide plus one and a half times carbon dioxide in the reactor stream 128 is preferably 2.0. As a general rule no additional reactants are required. Alternatively, if the product is to be methane, the ratio of hydrogen to carbon monoxide preferably approaches but does not exceed 3.0. Similarly as a general rule no additional reactants will be required. However, any additional reactants desired may be passed via line 151.

A product is formed in the product reaction zone 150 by the reaction of reactants including hydrogen and carbon monoxide. A residual stream including residual hydrogen and carbon monoxide is also formed in the product reaction zone 150. As indicated, the ratio of hydrogen to other reactants in the product reaction zone is such as to facilitate the formation of the product. The product, by-product, and unconsumed reactants are removed as a mixed product stream from the product reaction zone 150 via line 152.

The mixed product stream is passed via line 152 to a second separation zone 180 where the product and residual stream are physically separated from the mixed product stream.

The second separation zone includes at least one membrane separator or other physical separating device and generally will also include at least one liquid separator. For example, if the desired product is methanol, then the second separation zone 180 will preferably include one or more condensers or other gas-liquid separating devices to remove methanol and water to produce a product stream which is passed via line 190. Alternatively, if methane is the desired product, then separation zone 180 will generally include one or more condensers to remove water vapor as condensate, and an acid gas unit to remove carbon dioxide, as well as a membrane separator.

The membrane separator or other physical separating device in the second separation zone 180 is used to form a second hydrogen stream formed by passing residual hydrogen and carbon monoxide through the separation membrane in the second separation zone 180.

At least a portion of the second hydrogen stream formed in second separation zone 180 is ultimately passed via line 127 for use as a recycle stream to the extent required for mixture with the first hydrogen stream passing via line 126. The extent of recycle is such as to maintain the ratio of hydrogen to carbon monoxide in the reacting stream 128 as it enters the product reaction zone 150 at the required stoichiometric ratio to facilitate the formation of the product in the product reaction zone.

The feed gas stream 100 has a ratio of hydrogen to carbon monoxide generally in the range of 0.5 to 3.0 depending upon the source of the feed gas. If the product is to be methane, then the ratio in stream 128 of hydrogen to carbon monoxide may be in the range of about 1.0 to about 3.0, preferably in the range of about 2.0 to 3.0 and most preferably in the range of 2.5 to 3.0. Alternatively, if the product desired is methanol, then the ratio in stream 128 of hydrogen to carbon monoxide is generally in the range of 1.5 to 2.5 and is preferably 1.9 to 2.1 and most preferably about 2.0 to 2.1. As carbon dioxide also takes part in the reaction to form methanol, the ratio of hydrogen to carbon monoxide is governed by the percentage of carbon dioxide present. For example, the ratio in stream 128 of hydrogen and carbon monoxide plus one and a half times carbon dioxide is preferably about 2.0 to 2.1.

The gas in the feed gas stream may comprise a number of other constituents besides hydrogen and carbon monoxide. For example, the gas in the feed gas stream may be a synthesis gas comprising hydrogen, carbon monoxide, carbon dioxide and nitrogen. Alternatively, the feed gas may contain in addition other components inert to the reaction processes. For example, the gas in the feed gas stream may also include hydrocarbons, helium, argon, and the like. However, compounds of sulfur are generally poisons to catalysts in the reaction zone, and in this case they must be removed prior to entering the reaction zone.

The pressure and temperature of the gas in the feed gas stream 100 is such as to facilitate separation in the first separation zone 120, as would be known to one skilled in the art having the benefit of this disclosure. For example, if the feed gas in the feed gas stream includes a mixture wherein the hydrogen to carbon monoxide ratio is 0.5, then the pressure may range from about 1500 psia to 200 psia, while the temperature may range from about 60° F. to 200° F.

The first separation zone includes at least one membrane separator and may include two or more membrane separators. For example, a spiral wound type membrane, or hollow fibre type membrane, might be employed in the first separation zone. However, as would be known to one skilled in the art having the benefit of this disclosure any one of a variety of membrane separators may be used to concentrate the available hydrogen relative to carbon monoxide to improve the hydrogen to carbon monoxide ratio in the first hydrogen stream by at least one and a half times and so facilitate formation of the desired product in the product reaction zone 150.

Alternatively, the first separation zone may include an appropriately engineered pressure swing adsorber system, as would be known to one skilled in the art having the benefit of this disclosure. However, it is believed that a membrane will generally be more preferable.

The hydrogen lean stream leaving the first separation zone 120 via line 122 will include some hydrogen. Further, depending upon the use of the hydrogen lean stream and the characteristics of the feed gas stream, the first separation zone may be operated to provide a hydrogen lean stream having particular characteristics. For example, where the hydrogen lean stream consists mainly of carbon monoxide, it may be used in downstream processes generally as effectively as gas streams produced in conventional processes. For example, the hydrogen lean stream 122 may be a non-permeate stream from a membrane separator consisting mostly or largely of carbon monoxide to be forwarded to a conventional power recovery unit including a gas turbine, heat recovery and steam generation sections and a steam turbine cycle.

The first hydrogen stream is passed via lines 126, 128, and 126a as appropriate to product reaction zone 150. The product reaction zone may include one or more of a variety of unit operations depending upon the product desired. For example, if methane is to be produced, then the product reaction zone 150 may include a number of methanator beds. In such a case, the first hydrogen stream 126 could be preheated to a temperature in the range of about 400° F. to 700° F. and fed at a pressure in the range of about 200 psia to 1500 psia to the first of a series of methanator beds where the methanation reaction proceeds exothermically. A portion of the reacting stream passing via line 128 could be directed to each of several methanators in series with the reaction product from each methanator being passed to each successive methanator to ultimately form a mixed product stream comprising of the desired product, methane, the by-products, carbon dioxide, and water, and residual hydrogen, and carbon monoxide, and any inert gases.

Alternatively, if methanol is the desired product, then the product reaction zone may include one or more methanol reactors. In such a case, the reactant stream would generally be at a pressure in the range of about 200 psia to 3000 psia and a temperature in the range of about 400° F. to 700° F. No steam or other reactants need be added. The resultant product stream includes the desired product methanol, and the by-products carbon dioxide and water, and residual hydrogen, and carbon monoxide, and any inert gases.

The mixed product stream passing via line 152 from the product reaction zone includes product, by-product, and unreacted feed. The mixed product stream would generally contain at least some condensible vapors and would generally include water.

The second separation zone includes at least one membrane separator or other physical separating device and will also generally and preferably contain at least one cooler and one liquid vapor separator to remove any condensible vapors in the mixed product stream prior to passage to one or more membrane separators in the second separation zone. For example, if the mixed product stream includes methane, carbon dioxide, water, and residual hydrogen and carbon monoxide, then the mixed product stream could be reduced in temperature to recover any water vapor as condensate. Further, any carbon dioxide could be subject to acid gas removal by conventional processes prior to passage of the remaining gases to a membrane separator or other physical separating device all as would be known to one skilled in the art having the benefit of this disclosure. Alternatively, if methanol was produced, then an approximate 95% methanol-water solution could be recovered by reducing the temperature of the mixed product stream including methanol, water, hydrogen, and oxides of carbon prior to passage of the mixed product stream to the membrane separator in the second separation zone 180. In this regard, it is preferable to provide one or more further removal stages such as water scrubbing, or refrigerated cooling and separating to insure that substantially all of the methanol is removed prior to passage to the membrane separator.

The gas passing through the membrane in the second separation zone is divided into two streams. The first is a second hydrogen stream which is relatively rich in hydrogen in relation to the amount of carbon monoxide By way of example, when methanol is produced in the product reaction zone, the ratio of hydrogen to carbon monoxide in the second hydrogen stream could be in the range of about 5 to 30. Alternatively, if methane were produced in the product reaction zone then the ratio of hydrogen to carbon monoxide might be in the range of 1 to 20.

The second stream produced may be the product stream if the product is a gas such as methane. If the product is a liquid, such as methanol, then the second stream recovered from the membrane separator or separators in the second separation zone will generally include the inert gases plus unconsumed reactants. By way of example, when methanol is produced in the product reaction zone, the remaining gases include carbon monoxide, hydrocarbons, some hydogen, and carbon dioxide, and inert gases, which are useful in combination as a low BTU gas.

The second hydrogen stream may be all or partially recycled as recycle stream 127 to help control the stoichiometric ratio of the reactants in the product reaction zone. By way of example, if methanol is produced in the product reaction zone as the desired product, then the second hydrogen stream might include hydrogen, and carbon monoxide in a ratio of about 5 to 30. Thus, if the first hydrogen stream 126 had hydrogen to carbon monoxide in a ratio of 1.5 to 2.0, then a sufficient portion of the second hydrogen stream could be recycled to bring the hydrogen to carbon monoxide plus one and a half times the carbon dioxide ratio in the reacting stream into the range of 2.0 to 2.1.

However, all or a portion of the second hydrogen stream need not be recycled depending upon process conditions and the product desired. For example, where methane is produced in a product reaction zone, a portion of the mixed product stream may be recycled after removal of liquids directly to the product reaction zone, thus minimizing the amount of the second hydrogen stream which must be recycled to obtain the advantages of the present invention.

Figure 2:
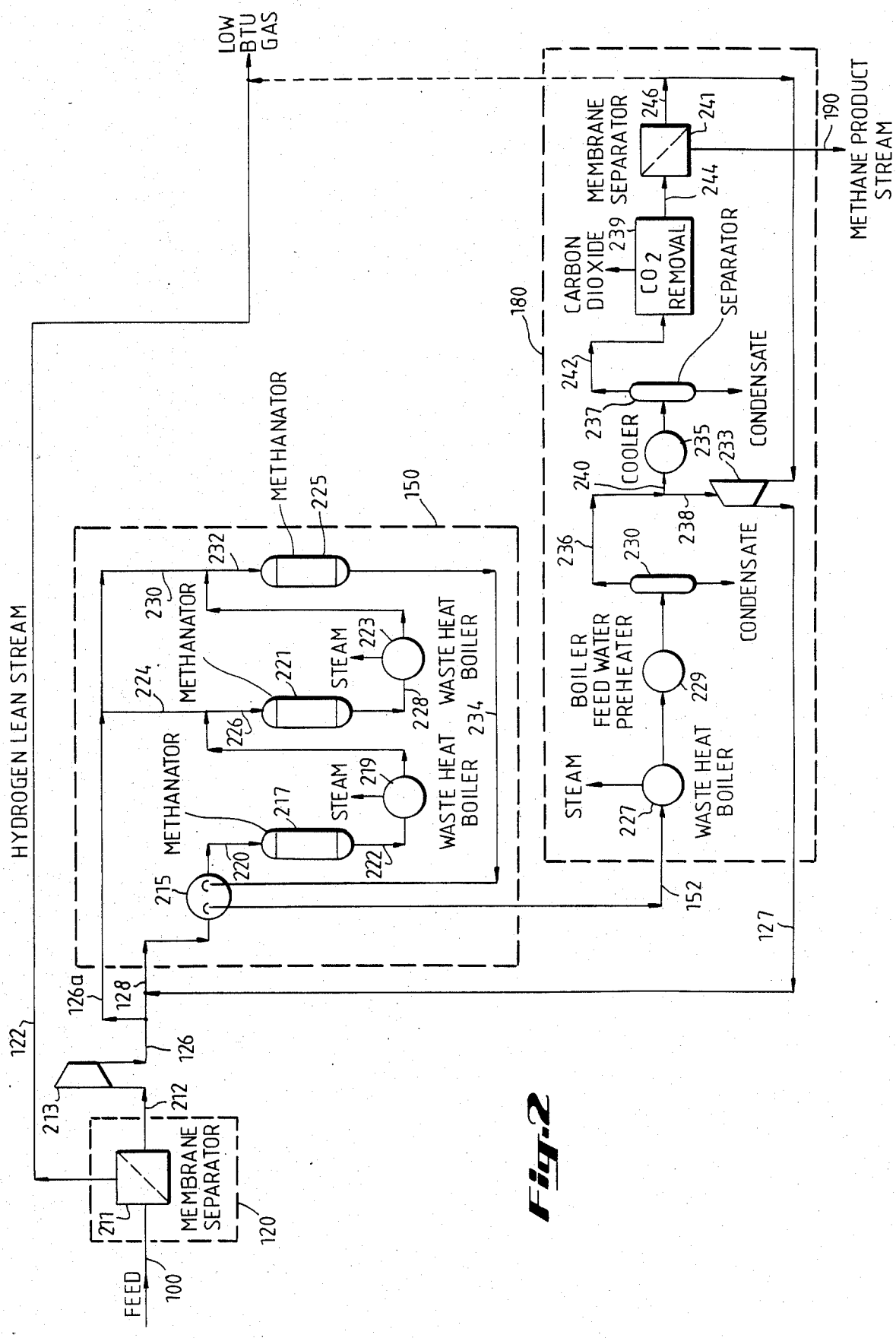
FIG. 2 is a flow diagram of a more particular embodiment of the present invention wherein methane is produced.
Figure 3:
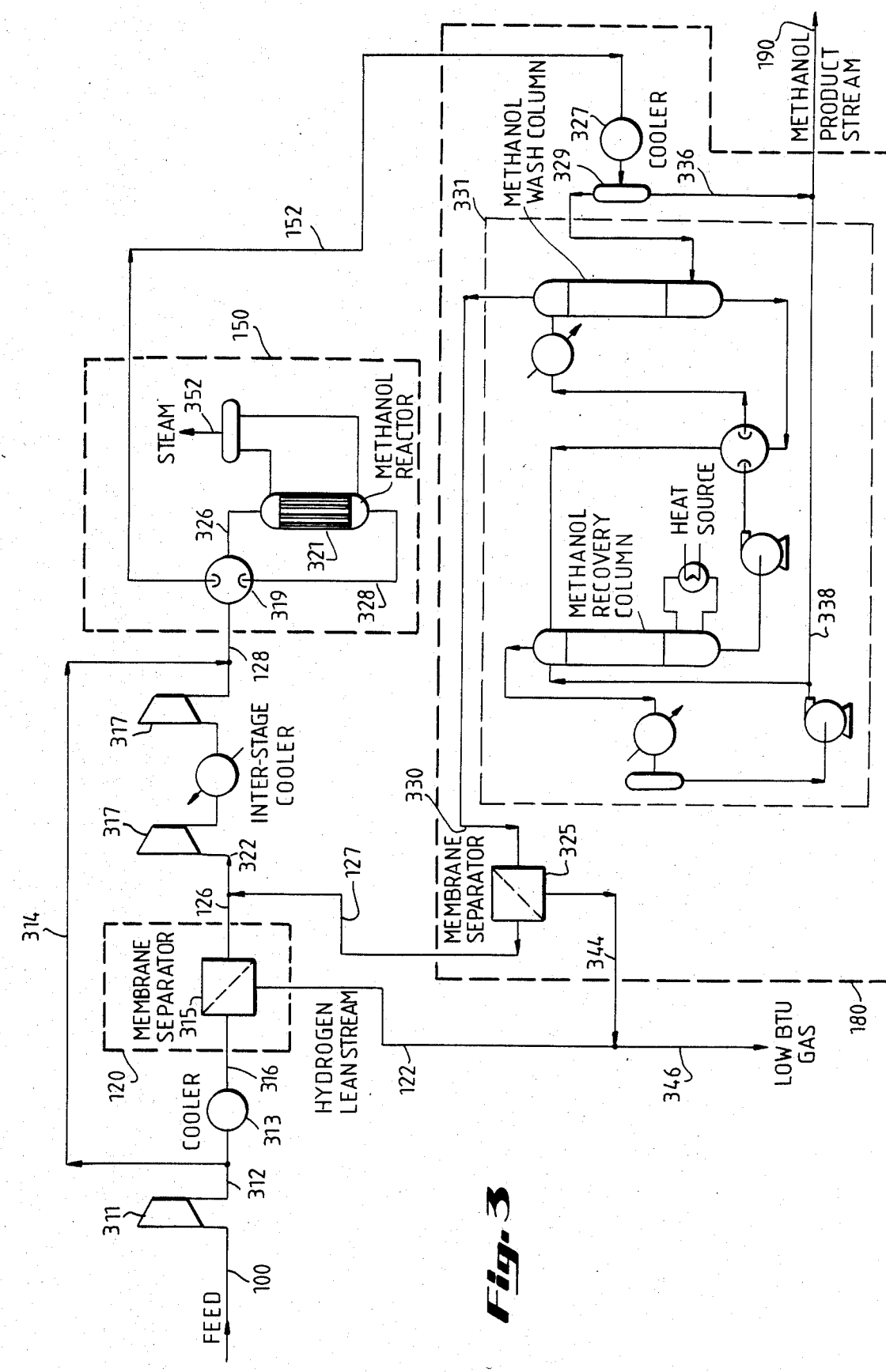
FIG. 3 is another embodiment of the present invention wherein methanol is produced.

Turning now to FIGS. 2 and 3, there will be discussed two more detailed embodiments of the present invention along with the results of certain computer related studies relating to these specific embodiments. These detailed embodiments will aid in demonstrating the usefulness and advantages offered by the subject invention and are to be taken by way of illustration rather than limitation.

Referring now to FIG. 2, there is shown a process for the co-production of substitute natural gas including methane and a low BTU gas useful in the generation of electric power. It was assumed that the feed gas stream 100 is made up of a synthesis gas produced in a British Gas/Lurgi coal gasifier and that any sulfur components along with any heavy oils and tars produced in the coal gasifier were removed, as for example by the Rectisol process. For a more detailed description of coal gasification in a British Gas/Lurgi coal gasifier followed by removal of certain components in a Rectisol process the reader's attention is invited to K. R. Tart and T. A. Rampling, "Methanation Key to SNG Success," Hydrocarbon Processing, April 1981 and A. L. Kohl and F. C. Riesenfeld, *Gas Purification*, pp. 748-52, which are hereby incorporated by reference.

A feed gas stream at 750 psia and 100° F. made up of feed gas containing about 29% hydrogen, 55% carbon monoxide, 7% methane, and 3.5% carbon dioxide, plus other components inert to the methanation reaction could be fed via line 100 to a membrane separator 211 where the hydrogen to carbon monoxide ratio could be improved to 1.71 in the permeate stream 212. The hydrogen to carbon monoxide ratio leaving in the non-permeate stream 122 should be 0.14.

The first hydrogen permeate stream 212 could then be compressed in compressor 213 to about 600 psia. The high pressure permeate would then provide a reactant stream in the form of fresh feed to each of three methanators, 217, 221 and 225. The total flow rate could be divided such that the first methanator receives 16.7%, the second 33.3% while the third receives the remaining 50%. The flow to the first methanator 217 could be joined by a recycle stream 127 from a recycle compressor 233. The combined or reacting stream 128 would be preheated in heat exchanger 215 to about 550° F.

The heating medium for raising the temperature of the combined feed in exchanger 215 to the first methanator 217 is supplied from the mixed product stream leaving the third methanator 225 via line 234.

The preheated gas passing via line 220 is fed to the first methanator 217 where the methanation reaction takes place. The reaction is exothermic resulting in a temperature of about 970° F. in the gas leaving the methanator via line 222. The methanators were presumed to be vertical vessels, containing a specific catalyst for the methanation reaction.

The hot gas leaving the first methanator 222 is cooled in a waste heat boiler 219 and is joined by the second portion of the reactant stream passing via line 224. The extent of cooling by waste heat boiler 219 is controlled such that the temperature of the combined gases in line 226 at the inlet to the second stage methanator 221 is maintained at 550° F.

The reaction is calculated to take place in the second methanator and result in a gas outlet temperature of 997° F. The hot gas passing via line 228 from the second methanator 221 is cooled in waste heat boiler 223 and is joined by the third portion of fresh feed passing via line 230. The extent of cooling by waste heat boiler 223 is controlled such that the temperature of the combined gases passing via line 232 at the inlet to the third methanator 225 is maintained at 500° F.

Final bulk methanation occurs in the third stage methanator 225. The temperature of the gas in line 234 leaving the reactor is 1063° F. The hot gas is cooled in a series of heat exchangers. First in heat exchanger 215 against incoming feed to the first stage reactor 217, then in a waste heat boiler 227, and finally in a boiler feed water preheater 229. The condensate that drops out as a result of the cooling is separated in vessel 231.

The cooled gas stream 236 is divided such that 65% is recycled to the first stage methanator via line 127 by the second stage of the two stage recycle compressor 233. The remaining gas is passed via stream 240 to be cooled in a cooler 235, and form a saturated gas and a condensate which is separated in vessel 237. Carbon dioxide is removed from the saturated gas leaving vessel 237 in line 242. Carbon dioxide removal may be accomplished in a suitable commercially available acid gas system 39, as would be known to one skilled in the art having the benefit of this disclosure.

Unreacted carbon monoxide and hydrogen in line 244 are removed from the methanated gas by permeation through a second set of membrane separators 241. The permeate stream in line 246 contains hydrogen and carbon monoxide which could be added to the non-permeate stream in line 122 from the first set of membrane separators 211 to increase the flow to a second process. Alternately, stream 246 could be added to the recycle stream 127, in which case the unconverted reactants could be recycled using the two stages of the two stage recycle compressor 233 to improve the overall yield of methane. A product in the form of a synthetic natural gas passes via line 190 as the non-permeate from the second set of membrane separators 241.

A computer simulation was performed following the process flow shown in FIG. 2 and the various conditions stated above but with the flow in stream 246 joining stream 122 rather than being recycled to compressor 233. The simulation was carried out using "Design/2000" simulation program from ChemShare Inc., 3000 Post Oak Blvd., Houston, Tex. The results along with estimated values are tabulated in Table 1.

TABLE 1

| | LB-MOLES/HR STREAM NUMBERS | | | | | | | | | |
|---|---|---|---|---|---|---|---|---|---|---|
| Component | 100 | 212 | 122 | 126 | 127 | 220 | 222 | 224 | 226 | 228 |
| Hydrogen | 2899 | 2319 | 580 | 387 | 249 | 635 | 129 | 644 | 773 | 176 |
| CO | 5545 | 1353 | 4192 | 226 | 228 | 454 | 148 | 376 | 524 | 166 |
| Methane | 717 | 125 | 592 | 21 | 1875 | 1896 | 2101 | 35 | 2136 | 2379 |
| Ethane | 81 | 9 | 71 | 2 | 0 | 2 | 0 | 3 | 3 | 0 |
| Nitrogen | 444 | 63 | 381 | 11 | 119 | 130 | 130 | 18 | 147 | 147 |
| CO2 | 316 | 198 | 118 | 33 | 1108 | 1141 | 1244 | 55 | 1299 | 1419 |
| Water | 21 | 19 | 2 | 3 | 186 | 190 | 289 | 5 | 294 | 413 |
| TOTAL | 10023 | 4086 | 5936 | 683 | 3765 | 4448 | 4041 | 1136 | 5176 | 4700 |
| TEMP (°F.) | 100 | 80 | 100 | 309 | 283 | 550 | 970 | 309 | 550 | 978 |
| PRESS (PSIA) | 750 | 250 | 740 | 600 | 620 | 600 | 595 | 600 | 575 | 570 |
| Component | 230 | 232 | 234 | 236 | 238 | 240 | 242 | 244 | 246 | 190 |
| Hydrogen | 1288 | 1464 | 385 | 386 | 251 | 135 | 135 | 135 | 115 | 20 |
| CO | 752 | 918 | 353 | 354 | 230 | 124 | 124 | 124 | 37 | 87 |
| Methane | 69 | 2449 | 2869 | 2863 | 1861 | 1002 | 1002 | 1002 | 200 | 802 |
| Ethane | 5 | 5 | 0 | 0 | 0 | 0 | 0 | 0 | 0 | 0 |
| Nitrogen | 35 | 182 | 182 | 182 | 118 | 64 | 64 | 64 | 8 | 56 |
| CO2 | 110 | 1530 | 1684 | 1983 | 1094 | 589 | 589 | 20 | 5 | 15 |
| Water | 10 | 423 | 678 | 285 | 185 | 99 | 1 | 1 | 1 | 0 |
| TOTAL | 2269 | 6971 | 6152 | 5753 | 3739 | 2013 | 1915 | 1346 | 366 | 980 |
| TEMP (°F.) | 309 | 500 | 1063 | 230 | 230 | 230 | 100 | 100 | 90 | 100 |
| PRESS (PSIA) | 600 | 550 | 545 | 485 | 485 | 485 | 480 | 470 | 200 | 460 |

The calculated results set forth in Table 1 highlight a number of advantages believed to be provided by the present invention as set forth in the specific embodiment described. For example, the gas leaving the third methanator 225 via line 234 is generally unsuitable to send to the pipeline as natural gas, even on a carbon dioxide and water free basis. This is due to the high levels of unreacted hydrogen and carbon monoxide still in the gas with the methane.

The traditional solution to removing these undesirable gas components from a synthetic natural gas stream is to cool the hot gas to remove most of the steam as condensate, reheat the gas to reaction temperature, and then react the carbon monoxide and hydrogen together in the gas to form more methane in a final methanation step. Pipeline quality gas is achieved after carbon dioxide removal and dehydration steps are taken to meet the pipeline requirements.

However, further economy to the process is achieved by utilizing membrane separators 241 for the separation of the unconsumed hydrogen and carbon monoxide from the methane. As discussed with regard to the foregoing embodiment, this may be achieved by cooling the hot gas leaving the third bulk methanator 225, removing the condensed water vapor then removing the carbon dioxide in an acid gas removal system 239. At this point the membrane separators 241 are used to separate hydrogen, and residual water vapor, carbon monoxide, and carbon dioxide from methane, which is left in a non-permeate stream 190.

The separated permeate constituents are suitable for adding directly to a gas turbine feed in an electrical power recovery unit or in recycling to join the first hydrogen stream downstream from the first set of membrane separators 211. This in turn results in an overall increase in methane yield.

Further a process in accordance with the foregoing specific embodiment allows for the reduction, or total elimination, of the CO shift reactor and associated equipment such as a waste heat recovery unit, steam producing equipment, and water treating facilities in the SNG production step. Still further, the capacity of the acid gas treating unit for carbon dioxide removal is much smaller than would be required under conventional processes. This in turn results in savings of capital investment.

The foregoing embodiment may also take advantage of a second process such as cogeneration, or power generation by combined cycle to use the large flow of hydrogen lean gas produced from the first separating zone. The combination of producing both SNG and power from one facility is very likely.

Consequently, it can be seen with regard to the foregoing that the improvement to the hydrogen to carbon monoxide ratio in the reactant stream makes it possible to react the hydrogen with the carbon monoxide directly in a series of bulk methanation reactions and thus eliminate the need for a separate CO shift reactor upstream from a methanation step. The non-permeate stream from the first separation zone can be used as the feed to a second process such as combined cycle power generation. The combination of the two processes when optimally designed uses less equipment, and less energy than the sum of the individual processes.

Hydrogen, carbon monoxide, and water vapor from the second hydrogen rich stream may be recycled to the first methanator for improvement in the overall methanation yield or may be added to the first hydrogen lean stream upstream from the second process to increase the production of the second process. In either case the requirement for a conventional final methanation step prior to the acid gas treating unit is eliminated.

Turning now to FIG. 3, there is shown another embodiment of the present invention. Again, for illustrative purposes it was assumed that a synthesis gas was produced in a British Gas/Lurgi coal gasifier and that sulfur and heavy oils are removed in a Rectisol process.

A feed gas stream made up of feed gas containing about 28.9 mole % hydrogen, 55% carbon monoxide and 3.5% carbon dioxide, plus oher components inert to the methanol synthesis reaction could be fed via line 100 and compressed from about 450 psia to 750 psia in a single stage compressor 311. The major part of the flow in line 312 could be cooled to ambient temperature in a gas cooler 313 and fed to a set of membrane separators 315 where the hydrogen to carbon monoxide ratio could be increased to 1.7 in the first hydrogen stream leaving as a permeate via line 126. The balance of the gas flow 314 could by-pass the cooler and the membranes, thus allowing better control on the resultant composition ultimately being fed to the methanol synthesis reactor in product reaction zone 150.

The first hydrogen stream 126 is joined by a second hydrogen stream in line 127 coming from another membrane separation unit 325, located in the second separation zone downstream from the methanol synthesis reactor. The combined permeate stream 322 is then recompressed to about 750 psia in the booster compressor 317, joined by gas from line 314, preheated to the reaction temperature of 445° F. in heat exchanger 319, and then fed to the methanol synthesis reactor 321 in a product reaction zone.

The type of reactor used in this example is similar to Lurgi's, where the heat of reaction evolved in the reactor is removed in line 352 by generating medium pressure steam. As would be recognized by one skilled in the art having the benefit of this disclosure, an alternative method of moderating reaction temperature, for example, by cold gas quench, would also prove to be effective in conjunction with this embodiment of the invention.

Hot gas passing via line 328 from the synthesis reactor 321 should approach to within 50° F. of equilibrium temperature though the exact temperature of approach will depend on the activity of the catalyst used in the reactor. The gas in line 328 contains about 7.6 mole percent methanol, and is cooled by back exchanging it against the feed to the reactor in heat exchanger 319. Final cooling to ambient temperature is achieved in a water cooler 327, where most of the methanol, and some of the water produced in the reaction is condensed. The condensate containing about 95 percent methanol passes via line 336 and is separated in separator 329.

Vapor from the separator 329 is first scrubbed with water to remove the final traces of methanol. Those skilled in the art will recognize with the benefit of this disclosure that equipment 331 bounded within the broken line is a water wash, followed by methanol and water recovery in a conventional distillation step.

The vapor is fed via line 330 to a second set of membrane separators 325. The vapor is preferably substantially methanol free, since some membrane separators are believed to be adversely affected by methanol. However, if another separating device or a less sensitive membrane is employed, the vapor may include greater amounts of methanol.

The permeate stream 127 from the membrane separators 325 recovers much of the unused hydrogen from the reaction step and recycles it to the synthesis reactor via line 322 by booster compressor 317. The composition of permeate stream 127 is approximately 87% hydrogen, 5% carbon monoxide, and 7% carbon dioxide, plus other components inert to the methanol synthesis reaction.

A product in the form of a methanol solution passes via line 338 from the scrubbing step and is recovered by conventional distillation and then combined with the product rundown in line 336 from separator 329. The combined stream 190 contains approximately 95% methanol, 5% water, 900 ppm methyl formate, 700 ppm ethanol, and 150 ppm dimethylether. These latter trace quantities of components are produced by unwanted side reactions in the methanol synthesis reactor. The crude methanol could be refined for use as a chemical feedstock, or is stored as the crude product which is suitable for use as fuel.

The non-permeate streams 122 and 344 from both sets of membrane separtors 315 and 325 are combined and are essentially available at about 700 psia. The combined stream 346 contains about 20% hydrogen, and 60% carbon monoxide, with the remainder comprising methane, and carbon dioxide, plus other components. The gross heating value of the combined non-permeate streams is 366 BTU per standard cubic foot (SCF) with a net heating value 349 BTU/SCF. This stream is suitable for use in a standard gas turbine after pressure letdown as would be known to one skilled in the art having the benefit of this disclosure.

A computer simulation was performed following the process flow diagram shown in FIG. 3 and the various conditions stated above in regard to the foregoing embodiment. As with the embodiment shown in FIG. 2, the simulation was carried out using "Design/2000" simulation program from ChemShare Inc., 3000 Post Oak Blvd., Houston, Tex. The results along with estimated values are tabulated in Table 2.

TABLE 2

| Component | LB-MOLES/HR STREAM NUMBERS | | | | | | | | | | | |
|---|---|---|---|---|---|---|---|---|---|---|---|---|
| | 100 | 314 | 316 | 122 | 126 | 326 | 328 | 127 | 190 | 330 | 344 | 346 |
| Hydrogen | 2253 | 361 | 1893 | 379 | 1514 | 5099 | 4083 | 3228 | | 4035 | 807 | 1186 |
| CO | 4310 | 690 | 3621 | 2737 | 883 | 1762 | 1264 | 189 | | 1269 | 1080 | 3817 |
| Methane | 557 | 89 | 468 | 387 | 81 | 189 | 189 | 19 | | 190 | 171 | 558 |
| Ethane | 63 | 10 | 53 | 47 | 6 | 17 | 17 | 1 | | 17 | 16 | 63 |
| Nitrogen | 345 | 55 | 290 | 249 | 41 | 104 | 104 | 8 | | 105 | 97 | 345 |
| CO2 | 267 | 43 | 224 | 84 | 141 | 451 | 445 | 265 | | 447 | 181 | 265 |
| Methanol | 0 | 0 | 0 | 0 | 0 | 0 | 504 | 0 | 501 | 0 | 0 | 0 |
| Water | 16 | 3 | 14 | 1 | 12 | 23 | 29 | 8 | 26 | 8 | 0 | 2 |
| TOTAL | 7811 | 1251 | 6563 | 3884 | 2678 | 7645 | 6635 | 3718 | 527 | 6071 | 2352 | 6236 |
| TEMP (°F.) | 100 | 250 | 100 | 100 | 93 | 445 | 495 | 98 | 100 | 100 | 100 | 99 |
| PRESS (PSIA) | 470 | 750 | 740 | 740 | 250 | 730 | 725 | 250 | 710 | 710 | 710 | 710 |

The calculated results set forth in Table 2 highlight a number of advantages believed to be provided by the present invention as set forth in the specific embodiment described above. For example, there results a more economical co-production of methanol and power, since the carbon monoxide rich stream could be effectively utilized directly to cogenerate electrical power and steam or in a combined cycle for electrical power. Alternatively, the carbon monoxide stream could be purified, whereby both methanol and carbon monoxide could be used as chemical intermediaries to produce other products such as methyl acetate, an industrially useful chemical.

In conventional processes a shift reaction is used to adjust the content of the feed gas and obtain a proper ratio of reactants to produce methanol. This adjustment step is a source of inefficiency to the process due to the consumption of carbon monoxide, the requirement for steam, and the load on the acid gas treating section in removing excess carbon dioxide.

Further, in a conventional process the production of methanol leaving the methanol reactor is limited to around 5% due to an unfavorable equilibrium. As a result, it is understood that commercial operations employ a large recycle stream around the reactor to conserve synthesis gas. The recycle stream has the effect of building up a concentration of components inert to the reaction, which causes a limit to the amount of recycle possible.

A purge stream from the synthesis loop is required in conventional processes to limit the build up of inerts. The purge stream not only removes the undesirable inert components, but also represents a loss of the feed components. A purge rate is selected that hopefully maximizes overall production of methanol at acceptable costs.

Although membrane separators have been used to recover hydrogen and carbon monoxide from the purge stream from the reaction recycle loop and the hydrogen/carbon monoxide mixture routed back to the feed, to produce what is said to be an overall improvement in efficiency to the process, they have not been used, as provided herein to recover the unreacted reactants from the loop while rejecting all the inert compounds and thus improving the equilibrium in favor of greater methanol production per pass through the reactor.

Further, the foregoing embodiment allows for the reduction, or in some cases, the total elimination of the CO shift reaction, and related equipment such as CO shift reactor, waste heat recovery unit, steam producing equipment, and water treating facilities. Furthermore, the capacity of the acid gas treating unit for any carbon dioxide removal is substantially reduced, or, as in this case is not required, depending on the composition of the synthesis gas.

The following examples are provided to further illustrate the subject invention in conjunction with the foregoing embodiments. As with, the detailed embodiments, these examples are provided by way of illustration rather than limitation.

EXAMPLE 1

Two complete design simulations were carried out on the ChemShare program to compare the efficiency of the embodiment generally shown in FIG. 3 when co-producing methanol and a low BTU gas with a competing process using a conventional technique. The total feed gas composition and feed rate, and the methanol production rate on both processes were fixed at the same amount or as close as permitted by program convergence tolerances.

In the conventional process a portion of the total feed gas available was used to produce methanol, while the remainder was utilized as part of the low BTU gas. A portion of the feed gas needed for the production of methanol was made to by-pass the shift section while the rest was shifted to produce the necessary additional hydrogen required for the desired methanol production rate. The by-passed feed was combined with the shifted gas and the mixture compressed to about 760 psia.

The gas after cooling was treated by an acid gas treating unit to remove the carbon dioxide content down to 3% volume. The resultant gas mixture, after adding the recycled gas, comprised the reactants of hydrogen, carbon monoxide, and carbon dioxide in their correct stoichiometric ratio for the optimum production of methanol. The methanol reactor type used in this comparison was the Lurgi type as used in the embodiment described above.

After the methanol reaction, condensable components were removed by cooling and separation. Ninty-five percent of the noncondensed components were recycled to the feed of the reactor downstream from the acid gas treating unit. The remaining five percent was determined to be the optimum purge rate from the methanol loop after several simulation runs with the purge rate being varied from 1% to 90%. Finally the purge gas was added to the major low BTU gas stream.

The conventional process with a shift reaction was compared with an embodiment as per FIG. 3 with the addition of a gas expander. The expander is designed to recover some of the energy from the high pressure non-permeate streams in the lean hydrogen stream such as the low BTU gas stream. The gas expander was presumed to be located downstream on stream 346 shown in FIG. 3.

The comparison was made on a cold gas efficiency basis using the total lower heating value of feeds and products and after making adjustments for the energy credits and debits such as steam and electrical power. All forms of energy were converted to a million BTU per hour basis.

The amount of energy required to remove the produced carbon dioxide in the acid gas treating unit in the conventional process varies depending on which process is selected. The most energy efficient processes for treating acid gases at conditions of composition and pressure found in this illustrative example are proprietry processes. Therefore for the purposes of this comparison the energy required to remove carbon dioxide to the extent necessary was set equal to zero. However, it will be recognized by one skilled in the art that energy must be expended to cause a reduction in entropy in the process of separating a gas.

The calculated results of the comparison are shown in Table 3.

TABLE 3

| OVERALL COLD GAS EFFICIENCY RESULTS | | |
|---|---|---|
| | Conventional Process | Modified Process Generally as per FIG. 3 |
| FEED: | 991.23[1] | 991.23 |
| PRODUCTS: | | |
| Methanol (Liquid) | 166.27 | 167.02 |
| Low BTU Gas | 766.93 | 782.56 |
| Steam (from Methanol Reactor) | 17.97 | 22.35 |
| CONSUMPTIONS: | | |
| $CO_2$ Removal | $(0^2)$ | (—) |
| Make up Steam (for shift reaction) | (15.04) | (—) |
| Net Compression | $(4.89^3)$ | $(14.53^3)$ |
| | 931.24 | 957.40 |
| COLD GAS EFFICIENCY | $\frac{931.24}{991.23} \times 100 =$ | $\frac{957.40}{991.23} \times 100 =$ |

TABLE 3-continued
OVERALL COLD GAS EFFICIENCY RESULTS

| | Conventional Process | Modified Process Generally as per FIG. 3 |
|---|---|---|
| | 93.9% | 96.6% |

[1] All figures in million BTU's. Per hour figures for feed and products are on a lower heating value basis, while consumption figures are in terms of million BTU's per hour.
[2] Assumed value.
[3] Heat equivalent of mechanical energy based on 1 HP-Hr = 2,545 BTU's.

EXAMPLE 2

As will be known to those skilled in the art having the benefit of this disclosure, the greater the proportion of methanol produced the more inefficient the co-production of methanol and low BTU gas becomes, since either physical separation or shift reaction is required to facilitate production of methanol. For the extreme of no methanol production the efficiency of the overall process is 100%, whether shift reaction or physical separation is used, since the product low BTU gas rate in BTU's per hour is identical to the feed rate. With this in mind another comparison of the methanol production efficiencies of the different processes can be made.

The efficiency attributable to a fixed amount of methanol production in a conventional process using a shift reactor is that efficiency which when combined with the 100% efficiency of the low BTU gas results in an overall efficiency equal that of the overall process. The same is true for the embodiment illustrated in Example 1.

Therefore, if one sets the feed to each process as the same and also sets the amount of methanol produced as the same, a new energy balance for the production of methanol can be isolated, thus allowing a comparison of the two processes as their efficiencies relate to methanol production. The results of such a comparison derived from the results shown in Table 3 are given in Table 4.

TABLE 4
METHANOL PROCESS COLD GAS EFFICIENCY RESULTS

| | Conventional Process | Modified Process Generally as per FIG. 3 |
|---|---|---|
| FEED: | 991.231–766.93 | 991.23–766.93 |
| PRODUCTS: | | |
| Methanol (Liquid) | 166.27 | 167.02 |
| Low BTU Gas | — | 782.56–766.93 |
| Steam (from Methanol Reactor) | 17.97 | 22.35 |
| CONSUMPTIONS: | | |
| $CO_2$ Removal | (0) | (—) |
| Make up Steam (for shift reaction) | (15.04) | (—) |
| Net Compression | (4.89) | (14.53) |
| | 164.31 | 190.47 |
| COLD GAS EFFICIENCY ATTRIBUTED TO METHANOL PRODUCTION | $\frac{164.31}{224.3} \times 100 =$ 73.3% | $\frac{190.47}{224.3} \times 100 =$ 84.9% |

Therefore the efficiency of the methanol production portion of the process shown in FIG. 3 and described above is $84.9/73.4 \times 100 = 116\%$ more efficient as compared to the methanol production portion of the conventional process even excluding any allowance for carbon dioxide removal in the conventional process.

It is recognized that heat cannot be converted into power at 100% efficiency. The inefficiency of the heat conversion necessary for net compression will erode some of the calculated energy advantages in efficiency for the methanol production. However, it is believed that energy savings result. Further, as the foregoing examples and calculations indicate, a process according to the present invention minimizes or eliminates several disadvantages in prior processes. For example, the CO shift reactor, its associated equipment, and the acid gas treating unit has been eliminated resulting in an overal reduction in capital investment.

Although the foregoing discussion and description is limited to methane and methanol synthesis reactions in the product reaction zone it is also believed that the process of the present invention may be advantageously applied to the production and purification of hydrogen. In this case the first hydrogen stream would be made to bypass the steam reformer, while the hydrogen lean stream would be reformed with steam. After reforming, the two streams would be combined and shifted in a conventional shift reactor as the product reaction zone to produce more hydrogen. The by-product carbon dioxide would be removed by conventional acid gas removal processes and the resultant stream fed to a second separation zone providing for a more pure hydrogen stream from the second hydrogen rich stream.

Further, a number of variations and changes may be made to the various processes described above and still fall within the spirit and framework of the present invention. For example, where methane is produced according to the embodiments described with respect to FIG. 2, a final methanator along with its associated heat exchangers and other equipment may be substituted for one or more of the membranes 41 used in the second separation zone. Additionally, where methanol is produced in accordance with the embodiments described in conjunction with FIG. 3, there may be substituted a methanol synthesis reactor which is cooled by cold feed injection within the reactor bed. Alternatively, with respect to the two embodiments disclosed above as well as other embodiments of the present invention, variations may be made in operating conditions, including pressure, temperature and various recycle and other flow rates while still remaining within the spirit and framework of the present invention, as would be known to one skilled in the art having the benefit of this disclosure.

Further modifications and alternative embodiments of the inventive methods disclosed herein will be apparent to those skilled in the art in view of this disclosure. Accordingly, this description is to be construed as illustrative only and is for the purpose of teaching those skilled in the art the manner of carrying out the invention. It is understood that the forms the invention shown and described are to be taken as illustrative embodiments. Various changes may be made in the arrangement of the steps or materials used. For example, equivalent materials may be substituted for those illustrated and described herein and certain features of the invention may be utilized independently of the use of other features. All this would be apparent to one skilled in the art after the benefit of this description of the invention.

What is claimed is:

1. A process for producing methanol from a feed gas comprising:

passing at least a portion of the feed gas stream comprising hydrogen plus carbon monoxide and carbon dioxide to a first separation zone, the ratio of hydrogen to carbon monoxide and carbon dioxide in said feed gas stream being insufficient for effective methanol production;

physically separating the feed gas stream in the first separation zone into a first hydrogen stream wherein the ratio of hydrogen to carbon monoxide and carbon dioxide is greater than in the feed gas stream and a first product stream comprising a hydrogen lean stream rich in carbon monoxide wherein the ratio of hydrogen to carbon monoxide and carbon dioxide is less than in the feed gas stream;

passing the first hydrogen stream to a product reaction zone to form a mixed product comprising methanol formed by the reaction of the reactants comprising hydrogen plus carbon monoxide and carbon dioxide and also residual components comprising residual hydrogen and carbon monoxide and carbon dioxide, the ratio of hydrogen to other reactants in the product reaction zone being such as to facilitate the formation of methanol;

removing the methanol and residual components as a mixed product stream from the product reaction zone;

physically separating the methanol and residual components in the mixed product stream in a second separation zone into at least three separate streams including a product stream comprising methanol, a second hydrogen stream, said second hydrogen stream comprising hydrogen, and a second hydrogen lean stream;

using at least a portion of the second hydrogen stream together with any portion of the feed gas stream not passed to the first separation zone as appropriate to adjust the ratio of hydrogen to carbon monoxide and carbon dioxide in the product reaction zone to the desired ratio of reactants to facilitate the formation of methanol in the product reaction zone;

2. A process according to claim 1 wherein at least one of the first and second separation zones comprises at least one membrane separator.

3. A process according to claim 1 wherein at least one of the first and second separation zones comprises at least one pressure swing adsorber.

4. A process for producing methanol from a feed gas comprising:

passing at least a portion of a feed gas stream comprising hydrogen, carbon monoxide, and carbon dioxide and substantially free of sulphur to a first separation zone comprising one or more membrane separators, the ratio of hydrogen to carbon monoxide plus one-and-one-half times carbon dioxide in the feed gas stream being less than about 2.0 and the feed gas stream being at a pressure in the range of about 200 psia to 1500 psia;

separating the feed gas stream in the separation zone into a first hydrogen rich stream and a first hydrogen lean stream rich in carbon monoxide;

passing the first hydrogen rich stream to a product reaction zone at sufficient temperature and pressure to form a mixed product stream comprising methanol, water and any unreacted reactants including hydrogen and carbon monoxide, the ratio of hydrogen to carbon monoxide plus one-and-a-half times carbon dioxide being in the range of about 1.5 to about 2.5 to thereby facilitate the formation of methanol;

reducing the tmeperature on the mixed product stream to condense out methanol and water as a product and by-product stream and form a non-condensing stream comprising hydrogen, carbon monoxide, and any other non-condensible components;

substantially removing any remaining methanol from the non-condensing stream in a second separation zone and thereafter passing it through at least one membrane separator in the second separation zone to form a second rich hydrogen stream and a second lean hydrogen stream rich in carbon monoxide;

recycling at least a portion of the second hydrogen rich stream to the product reaction zone and using the second hydrogen rich stream and any portion of a feed gas stream not passed to the first separation zone to maintain the ratio of hydrogen to carbon monoxide plus one-and-a-half times carbon dioxide in the product reaction zone at a ratio of about 1.5 to about 2.5 to facilitate the formation of methanol in the product reaction zone 5. A process according to claim 4 wherein the ratio of hydrogen to carbon monoxide plus one and one-half times carbon dioxide is in the range of about 2.0 to 2.1.

6. A process according to claim 1 wherein the feed gas is obtained from a coal gasifier without being subjected to a carbon monoxide shift reaction.

7. A process for producing methanol from a feed gas comprising:

passing at least a portion of the feed gas comprising hydrogen and carbon monoxide to a first separation zone, the ratio of hydrogen to carbon monoxide in the feed gas being greater than about 0.5 but less than about 2.0;

physically separating the feed gas stream in the first separation zone into a first hydrogen stream wherein the ratio of hydrogen to carbon monoxide and carbon dioxide is greater than in the feed gas stream and a first product stream comprising a hydrogen lean stream rich in carbon monoxide wherein the ratio of hydrogen to carbon monoxide and carbon dioxide is less than in the feed gas stream;

passing the first hydrogen stream to a product reaction zone to form a mixed product comprising menthanol formed by the reaction of the reactants comprising hydrogen plus carbon monoxide and carbon dioxide and also residual components comprising residual hydrogen and carbon monoxide and carbon dioxide, the ratio of hydrogen to other reactants in the product reaction zone being such as to facilitate the formation of methanol;

removing the methanol and residual components as a mixed product stream from the product reaction zone;

physcially separating the methanol and residual components in the mixed product stream in a second separation zone into at least three separate streams including a product stream comprising methanol, a second hydrogen stream, said second hydrogen stream comprising hydrogen, and a second hydrogen stream;

using at least a portion of the second hydrogen stream together with any portion of the feed gas stream not pased to the first separation zone as appropriate to adjust the ratio of hydrogen to carbon monoxide and carbon dioxide in the product reaction zone to the desired ratio of reactants to facilitate the formation of methanol in the product reaction zone.

8. A process for producing methanol and a low-BTU gas from the output of a coal gasifier, said output comprising hydrogen and oxides of carbon including carbon monoxide, without the need for altering the ratio of hydrogen to oxides of carbon by means of chemical reactions such as the CO-shift reaction, the process comprising:

separating the feed gas stream in a first separation zone into a first hydrogen-rich stream and a first hydrogen lean, low-BTU gas stream enriched in carbon monoxide;

passing the first hydrogen rich stream to a product reaction zone under conditions to form in a product reaction process a product stream comprising methanol, water, compounds inert to the product reaction process, and unconsumed reactants including hydrogen and oxides of carbon;

reducing the temperature of the product stream sufficiently to form a cooled product stream comprising methanol condensate and uncondensed components including uncondensed methanol;

separating the methanol condensate from the said cooled product stream;

passing the uncondensed components in said cooled product stream through a second separation zone to form a second hydrogen-rich stream and a second hydrogen lean, low-BTU gas stream comprising oxides of carbon and substances inert to the methanol reaction; and, recycling at least a portion of the second hydrogen-rich stream to said product reaction zone so as to increase the mole ratio $H_2: (CO + 1.5 \, CO_2)$ in the product reaction zone thereby facilitating the formation of methanol in the product reaction zone.

9. A process according to claim 8 wherein any uncondensed methanol is substantially removed from the cooled product stream prior to passing said cooled product stream through the second separation zone.

10. A process according to claim 9 wherein at least one of the first and second separation zones comprises at least one pressure swing adsorber system.

11. A process according to claim 9 wherein at least one of the first and second separation zones comprises at least one membrane separator.

12. A method for producing methanol from a synthesis gas feed stream comprising carbon monoxide, carbon dioxide and hydrogen, but wherein the ratio of hydrogen to carbon monoxide is undesirably low for effective reaction to methanol, which comprises:

passing said feed stream into a first separation zone without a prior carbon monoxide shift reaction to concentrate said hydrogen into a first hydrogen-rich stream containing a grater ration of hydrogen to carbon monoxide than in said feed stream;

passing said first hydrogen-rich stream into a methanol product reaction zone to form mixed products including methanol, water and unreacted hydrogen;

removing said methanol and water from said mixed products to form a methanol product stream and residual mixed products;

passing residual mixed products following said removal of methanol and water into a second separation zone to concentrate hydrogen in said residual products to form a second hydrogen-rich stream; and, recycling a quantity of said second hydrogen-rich stream to said reaction zone sufficient to maintain a desirable ratio of hydrogen to carbon monoxide in said reaction zone.

* * * * *